US006433003B1

(12) United States Patent
Bobrove et al.

(10) Patent No.: US 6,433,003 B1
(45) Date of Patent: Aug. 13, 2002

(54) METHOD FOR TREATING HYPERHIDROSIS IN MAMMALS

(76) Inventors: Arthur M. Bobrove, 1539 Walnut Dr.; Jeffrey D. Urman, 1880 Hamilton Ave., both of Palo Alto, CA (US) 94303

(*) Notice: Subject to any disclaimer, the term of this patent is extended or adjusted under 35 U.S.C. 154(b) by 0 days.

(21) Appl. No.: 09/552,011

(22) Filed: Apr. 19, 2000

Related U.S. Application Data

(60) Provisional application No. 60/131,001, filed on Apr. 23, 1999.

(51) Int. Cl.[7] .............................................. A61K 31/40
(52) U.S. Cl. ...................................... 514/424; 514/969
(58) Field of Search ................................ 514/424, 969

(56) References Cited

U.S. PATENT DOCUMENTS

| | | |
|---|---|---|
| 2,956,062 A | 10/1960 | Lunsfoed |
| 3,943,242 A | 3/1976 | Fogel et al. |
| 4,096,254 A | 6/1978 | Benson et al. |
| 5,008,111 A | 4/1991 | Bodor |
| 5,155,045 A | 10/1992 | Cutler et al. |
| 5,223,528 A | 6/1993 | Hammer et al. |
| 5,258,388 A | 11/1993 | Hammer et al. |
| 5,462,950 A | 10/1995 | Fontana |
| 5,512,555 A | 4/1996 | Waldstreicher |
| 5,525,347 A | 6/1996 | Kellner et al. |
| 5,637,601 A | 6/1997 | Hammer et al. |
| 5,730,964 A | 3/1998 | Waldstreicher |
| 5,744,151 A | 4/1998 | Capelli |
| 5,744,463 A | 4/1998 | Bair |
| 5,962,505 A | * 10/1999 | Bobrove et al. ............. 514/424 |
| 6,093,414 A | 7/2000 | Capelli |

FOREIGN PATENT DOCUMENTS

| | | |
|---|---|---|
| CA | 1102345 | 6/1981 |

OTHER PUBLICATIONS

Abell and Morgan, "The treatment of idiopathic hyperhidrosis by glycopyrronium bromide and tap water iontophoresis" *British Journal of Dermatology* (1974) 91:87–91.
Atkin and Brown, (1996) "Treatment of Diabetic Gustatory Sweating with Topical Glycopyrrolate Cream" *Diabetic Medicine* 13:493–494.
Goldberg et al., (1994) "Transdermal Clonidine for Ameliorating Tamoxifeninduced Hot Flashes" *J. Clin. Onc.* 12:155–158.
Hays, (1978) "The Frey Syndrome: A Review and Double Blind Evaluation of the Topical Use of a New Anticholinergic Agent" *The Laryngoscope* 88:1796–1824.
Hays et al., (1982) "The Frey Syndrome: A Simple Effective Treatment" *Otolaryngol Head Neck Surg* 90:419–425.
Loprinzi et al., (1994) "Megestrol Acetate for the Prevention of Hot Flashes" *N. Engl. J. Med.* 331:347–351.
May and McGuirt, (1989) "Frey's Syndrome: Treatment with Topical Glycopyrrolate" *Head & Neck* 11:85–89.
Merck Index, Ninth Edition, Merck & Co., Rahway, NJ, p. 583, #4337 (1976).
Riolo, et al., *South Med. J.*, 83:1138–1143 (1990).
Schnider, et al., *Br. J. Dermatol.*, 136:548–552 (1997).
Shaw et al., (1997) "A Randomised Controlled Trial of Topical Glycopyrrolate, the First Specific Treatment for Diabetic Gustatory Sweating" *Diabetologia* 40:299–301.
Stegehuis and Ellis, (1989) "Treatment of Frey's Syndrome (Gustatory Sweating) with Topical Glycopyrrolate: Case Report" *NZ Med J.* 103(875):479.

* cited by examiner

*Primary Examiner*—Frederick Krass
(74) *Attorney, Agent, or Firm*—Burns, Doane, Swecker & Mathis L.L.P.

(57) ABSTRACT

This invention is directed to methods for treating hyperhidrosis in mammals. Specifically, the methods of this invention involve the topical administration of glycopyrrolate compounds to humans.

8 Claims, No Drawings

METHOD FOR TREATING HYPERHIDROSIS IN MAMMALS

CROSS-REFERENCE TO RELATED APPLICATIONS

This application claims the benefit of U.S. Provisional Application No. 60/131,001 filed on Apr. 23, 1999, which is incorporated by reference herein in its entirety.

BACKGROUND OF THE INVENTION.

1. Field of the Invention

This invention is directed to methods for treating hyperhidrosis in mammals. Specifically, the methods of this invention involve the topical administration of an effective amount of a glycopyrrolate compound to a mammal suffering from hyperhidrosis.

REFERENCES

The following publications, patent applications and patents are cited in this application:
1. Riolo et al., *South Med J.* 83:1138–1143 (1990)
2. Glogau R. G. *Cermatol. Surg.* 24:817–94 (1998)
3. Schnider et al., *Br. J. Dermatol.* 136:548–52 (1997)
4. Atkin et al., "Treatment of diabetic gustatory sweating with topical glycopyrrolate cream" *Diabetic Medicine* 13:493–494 (1996)
5. Shaw et al., "A randomized controlled trial of topical glycopyrrolate, the first specific treatment for diabetic gustatory sweating" *Diabetologia* 40:299–301 (1997)
6. May et al., "Frey's Syndrome: Treatment with topical glycopyrrolate" *Head & Neck* (January/February 1989) p.85–89
7. Col. Leonard L. Hays, "The Frey syndrome: A review and double blind evaluation of the topical use of a new anticholinergic agent" *The Laryngoscope* 88:1976 (1978)
8. *Remington's Pharmaceutical Sciences*, Mace Publishing Company Philadelphia Pa. 17$^{th}$ ed. (1985)
9. U.S. Pat. No. 5,525,347, Kellner et al.
10. U.S. Pat. No. 2,956,062, Lunsford et al.
11. Hays et al., "The Frey syndrome: a simple, effective treatment" *Otolaryngol Head Neck Surg.* 90:419–425 (1982)

All of the above publications, patent applications and patents are herein incorporated by reference in their entirety to the same extent as if each individual publication or patent was specifically and individually indicated to be incorporated by reference in its entirety.

2. State of the Art

Hyperhidrosis is an idiopathic pathological condition characterized by excessive, uncontrollable sweating beyond that required to cool the body. Disturbance of the central nervous system has been associated with this condition. It affects approximately one out of every one hundred people. Hyperhidrosis not only may result in intense social embarrassment, but also may even interfere with a person's occupation.

It most often involves one or several areas, especially the hands, axillae, feet or face, although it can even involve the whole body. Palmar hyperhidrosis is the most common form. Antiperspirants are generally ineffective in treating this form of perspiration. Oral medications are occasionally beneficial, but may have side effects. As a result, many persons with hyperhidrosis have resorted to a surgical procedure, endoscopic thoracic sympathectomy (1). Although the surgery affords permanent benefit in some 40% to 90% of affected individuals, it is invasive, requires general anesthesia and is not without potential side effects. As many as 50% of persons who have undergone thoracic sympathectomy develop compensatory and annoying sweating of the trunk or thighs.

More recently, botulinum A neurotoxin (BOTOX) which blocks the action on sweat glands of acetylcholine that is released by the autonomic nerves, has proven effective in hyperhidrosis. Minute amounts of BOTOX injected into the palms or axillae of affected individuals results in statistically significant benefit (2,3). The effect lasts for several months but requires repeat injections.

A non-invasive, convenient and effective treatment with few side effects would be a welcome alternative for treating hyperhidrosis.

Topical glycopyrrolate has been used previously to treat gustatory sweating associated with diabetic autonomic neuropathy (4, 5) In this disorder, sweating that often is profuse, begins soon after the patient ingests food, starting on the forehead and then involving the face, scalp and neck. A solution of glycopyrrolate was applied to the face of the patient which prevented the gustatory sweating.

Similarly, glycopyrrolate has also been used previously to treat gustatory sweating associated with Frey's syndrome which may develop after parotidectomy (11, 6, 7). Frey's syndrome is believed to result from the aberrant reinnervation of the sweat glands of the face by the severed parotid parasympathetic nerve fibers.

In both diabetic gustatory sweating and Frey's syndrome, the profuse facial sweating is induced by the specific stimulus of eating. Moreover, the sweating in each is a consequence of a distinct neuropathological process. In contrast, hyperhidrosis occurs spontaneously without a specific stimulus.

Glycopyrrolate administered with iontophoresis has been used to treat hyperhidrosis(8). In this case 0.1% of glycopyrrolate was administered topically to the skin and then the area of application was subjected to iontophoresis. For some patients, this treatment regime reduced the hyperhidrosis for up to 4 weeks. However, the patients needed to attend at the physicians office for the treatment and the treatment was associated with side effects such as abdominal discomfort and this treatment was not effective for all patients.

This invention is directed in part to the discovery that the daily topical application of a 0.25% to 6% glycopyrrolate compound to a mammal overcomes many of the prior problems in treating hyperhidrosis. Additionally, it provides advantages heretofore not achieved by conventional treatments for hyperhidrosis. For example, the glycopyrrolate compound to be applied does not have the side effects associated with Botox treatments or iontophoresis.

SUMMARY OF THE INVENTION

This invention is directed to methods for treating hyperhidrosis by the topical application of a composition comprising from about 0.25 to 6% by weight of a glycopyrrolate compound to a mammal.

This invention is directed to a method for alleviating hyperhidrosis in a mammal, which method comprises the steps of identifying a mammal susceptible to hyperhidrosis; and topically administering to the skin of said mammal a composition comprising from about 0.25% to 6% by weight of a glycopyrrolate compound. Preferably, the glycopyrrolate compound has formula I:

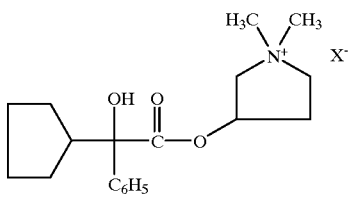

wherein X⁻ is a pharmaceutically acceptable counter ion salt.

This invention is also directed to a method for alleviating hyperhidrosis in a mammal, which method comprises the steps of identifying a mammal susceptible to hyperhidrosis; and topically administering to said mammal a pharmaceutical composition comprising from about 0.25 to 6% by weight of a glycopyrrolate compound and a pharmaceutically acceptable excipient. Preferably the glycopyrrolate compound has formula I:

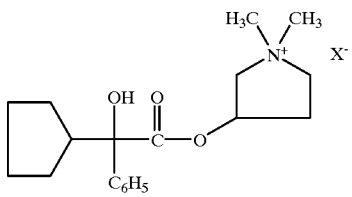

wherein X⁻ is a pharmaceutically acceptable counter ion salt.

DETAILED DESCRIPTION OF THE PREFERRED EMBODIMENTS

This invention is directed to methods for treating hyperhidrosis in a mammal by the topical application of a glycopyrrolate compound to a mammal.

Definitions

As used herein, the following terms have the following meanings;

The term "glycopyrrolate compound" means a compound of the formula:

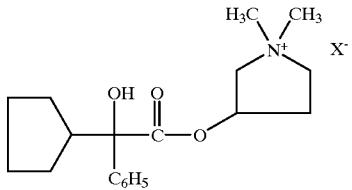

wherein X⁻ is a pharmaceutically acceptable counter ion salt.

The term "glycopyrrolate compound" also refers to analogues of glycopyrrolate capable of inhibiting hyperhidrosis wherein the chemical structure has been modified so as to introduce, modify and/or remove one or more functionalities of the structure. For example, such modification can result in the removal of an OH functionality, the introduction of an amine functionality, the introduction of a halo functionality, and the like. In so far as the glycopyrrolate analogues are capable of inhibiting hyperhidrosis they are encompassed by the definition of "glycopyrrolate compound".

Hyperhidrosis is a condition commonly known and understood by the average consumer who lacks any medical skill. It is an idiopathic condition characterized by excessive, uncontrollable perspiration beyond that required to cool the body.

The term "mammal" includes, without being limiting, such mammals as mice, rats, ovines, bovines and humans. Preferably the mammal is a human.

The term "therapeutically effective amount" means that amount of a drug or pharmaceutical agent that will elicit the biological or medical response of a tissue, system, animal or human that is being sought by a researcher, veterinarian, medical doctor or their clinician. In particular, with regard to treating the disorders of hyperhidrosis, the "therapeutically effective amount" is intended to mean that amount of the glycopyrrolate compound that will prevent or alleviate the hyperhidrosis.

The glycopyrrolate compound is effective over a wide dosage range and is generally administered in a therapeutically effective amount. Preferably the composition topically administered contains from 0.25% to 6% by weight and more preferably from 0.5% to 4% by weight of glycopyrrolate. It will be understood, however, that the amount of the glycopyrrolate actually administered may be determined by a physician in light of the relevant circumstances, including the condition to be treated, the chosen route of administration, the actual compound administered and its relative activity, the age, weight, and response of the individual patient, the severity of the patient's symptoms, and the like.

The compound is preferably administered topically. The daily dose of the compounds may vary depending on the medical condition of the patient, the skin status, and the age of the patient. Compounds of the present invention may be administered in a single daily dose, or the total daily dose may be administered in divided doses of two, three or four times daily. The compound may be applied to the hands, face, scalp, neck, trunk, back, limbs, axillae and/or groin of the human. Preferably, the glycopyrrolate compound is applied to the hands, face, neck, axillae or scalp of the human. Preferably, the glycopyrrolate is administered without the simultaneous or subsequent administration of iontophoresis to the skin.

Patients susceptible to hyperhidrosis include, but are not limited to, patients exhibiting idiopathic post stroke, central nervous system disease or injury resulting in hyperhidrosis.

The term "pharmaceutically acceptable counter salt" refers to salts which retain the biological effectiveness and properties of the glycopyrrolate compounds of this invention, which are not biologically or otherwise undesirable, and which carry an anionic charge. The glycopyrrolate compounds of this invention form salts by virtue of the presence of the quarternary ammonium thereon.

Pharmaceutically acceptable counter salts may be prepared from inorganic and organic acids. Salts derived from inorganic acids include hydrochloric acid, hydrobromic acid, hydrogen fluoride, hydrogen iodide, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The compounds of the present invention may be administered in a pharmaceutical composition comprising the active compound in combination with a pharmaceutically acceptable carrier adapted for topical administration. Topical pharmaceutical compositions may be in the form of a solution, cream, ointment, mousse, gel, lotion, powder or aerosol formulation adapted for application to the skin. These topical pharmaceutical compositions containing the compounds of the present invention ordinarily include from about 0.25% to 6.0% by weight of the active compound, more preferably from about 0.5% to 4% by weight of the active compound, in admixture with a pharmaceutically acceptable excipient.

"Pharmaceutically acceptable excipients" refers to compositions which retain the biological effectiveness and properties of the glycopyrrolate compounds of this invention and which are not biologically or otherwise undesirable.

Topical preparation containing the active compound can be admixed with a variety of carrier materials or pharmaceutically acceptable excipients well known in the art. When the excipient serves as a diluent, it can be a solid, semi-solid, or liquid, which acts as a vehicle, carrier or medium for the active ingredient. Thus, the compositions can be in the form of powders, suspensions, emulsions, solutions, syrups, alcoholic solutions, ointments, topical cleansers, cleansing creams, skin gels, skin lotions, mousses, roll-ons, aerosol or non-aerosol sprays in cream or gel formulations and soft gelatin capsules.

The compounds of the present invention may be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include alcohols, aloe vera gel, allantoin, glycerin, vitamin A and E oils, mineral oil, PPG2, myristyl propionate lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The glycopyrrolate composition may additionally contain one or more optional additives such as colorants, perfumes, etc. In practice, each of these optional additives should be both miscible and compatible with the glycopyrrolate compound. Compatible additives are those that do not prevent the use of the glycopyrrolate compound in the manner described herein.

Other suitable formulations for use in the present invention can be found in *Remington's Pharmaceutical Sciences* (8).

Methods

The methods of this invention comprise the topical application of a composition comprising 0.25% to 6% by weight of a glycopyrrolate compound to the skin surface of a mammal, which glycopyrrolate compound acts to inhibit hyperhidrosis.

The skin surface is preferably dried, and then a glycopyrrolate compound is applied to the skin surface of the human at the desired site. The compound can be applied to the hands, face, scalp, neck, trunk, back, limbs, axillae and/or groin of the human.

Sufficient amounts of the composition are employed to cover (i.e., coat) the entire skin surface with a layer of the glycopyrrolate compound. If necessary, excess glycopyrrolate compound can be removed from the skin with a wipe or tissue paper.

After application, the glycopyrrolate compound penetrates the skin very slowly and has been associated with few side effects (11,4,5). The glycopyrrolate is allowed to dry. Cosmetics can be applied over the glycopyrrolate.

Compositions

Glycopyrrolate is readily commercially available. Glycopyrrolate can be made as follows. α-phenylcyclopentaneglycolic acid is esterified by refluxing with methanol in the presence of hydrochloric acid and the resulting ester is transesterified with 1-methyl-3-pyrrolidinol using sodium as a catalyst. The transester is then reacted with methyl bromide to give glycopyrrolate (9,10).

Utility

It has been found that the application of glycopyrrolate to the skin of mammals suffering from hyperhidrosis reduces the unwanted perspiration at the location where the glycopyrrolate is applied.

EXAMPLES

Example 1

The patient is a 36 year old woman with a history of hyperhidrosis. She complained about profuse perspiration on her hands, feet, axillae and groin.

As a treatment, the patient was offered and consented to the application of 1% glycopyrrolate topical lotion, which she applied once daily in the evening to her palms.

The lotion consisted of 3 gm glycopyrrolate; 75 ml ethanol; 2.4 gm hydroxyethylcellulose; brought to a total volume of 300 ml with water and the pH adjusted to 2–4.5.

This treatment resulted in reduction in the perspiration associated with the hyperhidrosis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for alleviating hyperhidrosis in a mammal, which method comprises:
    a) identifying a mammal susceptible to hyperhidrosis; and
    b) topically administering to the skin of said mammal a composition comprising from about 0.25% to 6% by weight of a glycopyrrolate compound such that the hyperhidrosis is substantially reduced.

2. The method of claim 1 wherein the mammal is a human.

3. The method according to claim 2, wherein the glycopyrrolate compound is applied to the face and neck of the human.

4. The method according to claim 2, wherein the glycopyrrolate compound is applied to the palms of the human.

5. The method according to claim 1, wherein the glycopyrrolate compound has formula I:

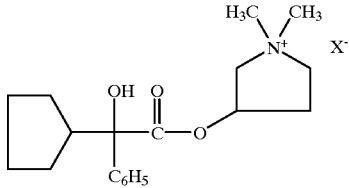

wherein X⁻ is a pharmaceutically acceptable counter ion salt.

6. A method for alleviating hyperhidrosis in a human, which method comprises:

a) identifying a human susceptible to hyperhidrosis; and b) administering to said human a pharmaceutical composition comprising from about 0.25% to about 6% by weight of a glycopyrrolate compound and a pharmaceutically acceptable excipient.

7. The method according to claim 6, wherein the glycopyrrolate compound has formula I:

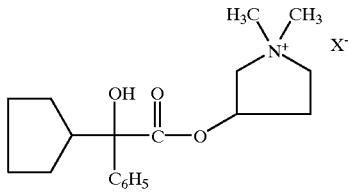

wherein X⁻ is a pharmaceutically acceptable counter ion salt.

8. The method according to claim 6 wherein the concentration of glycopyrrolate compound in the pharmaceutical composition is from 0.5% to 4.0% by weight.

* * * * *

(12) EX PARTE REEXAMINATION CERTIFICATE (4876th)
United States Patent
Bobrove et al.

(10) Number: US 6,433,003 C1
(45) Certificate Issued: Nov. 4, 2003

(54) METHOD FOR TREATING HYPERHIDROSIS IN MAMMALS

(75) Inventors: Arthur M. Bobrove, 1539 Walnut Dr., Palo Alto, CA (US) 94303; Jeffrey D. Urman, 1880 Hamilton Ave., Palo Alto, CA (US) 94303

(73) Assignees: Arthur M. Bobrove, Palo Alto, CA (US); Jeffrey D. Urman, Palo Alto, CA (US)

Reexamination Request:
No. 90/006,468, Nov. 29, 2002

Reexamination Certificate for:
| | |
|---|---|
| Patent No.: | 6,433,003 |
| Issued: | Aug. 13, 2002 |
| Appl. No.: | 09/552,011 |
| Filed: | Apr. 19, 2000 |

Related U.S. Application Data
(60) Provisional application No. 60/131,001, filed on Apr. 23, 1999.

(51) Int. Cl.[7] .............................................. A61K 31/40
(52) U.S. Cl. ........................................ 514/524; 514/969
(58) Field of Search ................................ 514/424, 969

(56) References Cited

PUBLICATIONS

Abell et al., The treatment of idiopathic hyperhidrosis . . . , British Journal of Dernatology(1974), vol. 91, pp. 87–91.*
Atkin et al., Treatment of Diabetic Glustatory sweating . . . , Diabetic medicine, 1996, vol. 13, pp. 493–494.*
Seukeran, D.C., et al. "The Use of Topical Glycopyrrolate in the Treatment of Hyperhidrosis" Clinical and Experimental Dermatology 1998: 23:204–205.

* cited by examiner

*Primary Examiner*—Marianne C. Seidel

(57) ABSTRACT

This invention is directed to methods for treating hyperhidrosis in mammals. Specifically, the methods of this invention involve the topical administration of glycopyrrolate compounds to humans.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

\* \* \* \* \*